United States Patent
Liang et al.

(10) Patent No.: US 11,699,513 B2
(45) Date of Patent: Jul. 11, 2023

(54) INFORMATION TRANSMISSION METHOD, APPARATUS, DEVICE AND MEDIUM FOR MEDICAL IMAGING APPLICATION

(71) Applicants: SHENZHEN INSTITUTES OF ADVANCED TECHNOLOGY CHINESE ACADEMY OF SCIENCES, Guangdong (CN); SHANGHAI UNITED IMAGING HEALTHCARE CO., LTD., Shanghai (CN)

(72) Inventors: Dong Liang, Guangdong (CN); Chao Zou, Guangdong (CN); Qiang He, Guangdong (CN); Guobin Li, Guangdong (CN); Qiang Zhang, Guangdong (CN); Xin Liu, Guangdong (CN); Hairong Zheng, Guangdong (CN)

(73) Assignees: SHENZHEN INSTITUTES OF ADVANCED TECHNOLOGY CHINESE ACADEMY OF SCIENCES, Guangdong (CN); SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 571 days.

(21) Appl. No.: 16/626,661

(22) PCT Filed: Dec. 29, 2018

(86) PCT No.: PCT/CN2018/125435
§ 371 (c)(1),
(2) Date: Dec. 26, 2019

(87) PCT Pub. No.: WO2020/107628
PCT Pub. Date: Jun. 4, 2020

(65) Prior Publication Data
US 2021/0335479 A1   Oct. 28, 2021

(30) Foreign Application Priority Data
Nov. 26, 2018 (CN) .......................... 201811417716.6

(51) Int. Cl.
*G16H 30/20* (2018.01)
*G16H 40/60* (2018.01)
(Continued)

(52) U.S. Cl.
CPC ............. *G16H 30/20* (2018.01); *G06F 21/31* (2013.01); *G16H 40/60* (2018.01); *G06F 3/1204* (2013.01)

(58) Field of Classification Search
CPC ........ G16H 30/20; G16H 40/60; G16H 40/40; G06F 21/31; G06F 21/629; G06F 3/1204
(Continued)

(56) References Cited

U.S. PATENT DOCUMENTS 8,321,240 B2 * 11/2012 Lorsch ................... G16H 20/10
705/2
10,491,575 B2 * 11/2019 Verzun ................ H04L 63/0464
(Continued)

FOREIGN PATENT DOCUMENTS

| CN | 101119517 A | 2/2008 |
| CN | 101799765 A | 8/2010 |

(Continued)

OTHER PUBLICATIONS

International Search Report and Written Opinion issued in connection with PCT/US2018/125435, dated Aug. 28, 2019, 9 pages.
(Continued)

*Primary Examiner* — Darryl V Dottin
(74) *Attorney, Agent, or Firm* — Duane Morris LLP

(57) ABSTRACT

Disclosed are information transmission method, apparatus, device and medium for medical imaging application. The
(Continued)

Determine an imaging device corresponding to an application authorization request according to the received application authorization request, and acquire an application permission profile of the imaging device — S110

Determine a medical imaging application corresponding to the imaging device according to the application permission profile of the imaging device, and transmit medical imaging application information corresponding to the medical imaging application to the imaging device — S110 method includes: an imaging device corresponding to an application authorization request is determined according to the received application authorization request, and an application permission profile of the imaging device is acquired; and a medical imaging application corresponding to the imaging device is determined according to the application permission profile of the imaging device, and medical imaging application information corresponding to the medical imaging application is transmitted to the imaging device.

20 Claims, 3 Drawing Sheets

(51) Int. Cl.
*G06F 21/31* (2013.01)
*G06F 3/12* (2006.01)

(58) Field of Classification Search
USPC .......................................................... 707/825
See application file for complete search history.

(56) References Cited

U.S. PATENT DOCUMENTS

| | | | |
|---|---|---|---|
| 11,410,753 B2* | 8/2022 | Khatri | H04N 7/185 |
| 2002/0174010 A1* | 11/2002 | Rice, III | G06F 16/182 |
| | | | 705/14.67 |
| 2014/0317615 A1 | 10/2014 | Ma et al. | |
| 2018/0204189 A1 | 7/2018 | Espinoza et al. | |

FOREIGN PATENT DOCUMENTS

| | | |
|---|---|---|
| CN | 101888416 A | 11/2010 |
| CN | 102129380 A | 7/2011 |
| CN | 105808274 A | 7/2016 |
| CN | 105978961 A | 9/2016 |
| CN | 108268270 A | 7/2018 |
| CN | 108565016 A | 9/2018 |

OTHER PUBLICATIONS

First Office Action dated Jul. 2, 2021 in corresponding Chinese Patent Application No. 201811417716.6.

* cited by examiner

INFORMATION TRANSMISSION METHOD, APPARATUS, DEVICE AND MEDIUM FOR MEDICAL IMAGING APPLICATION

CROSS-REFERENCE TO RELATED APPLICATIONS

This is a National Stage Application, filed under 35 U.S.C. 371, of International Patent Application No. PCT/CN2018/125435, filed on Dec. 29, 2018, which claims priority to Chinese patent application No. 201811417716.6 filed on Nov. 26, 2018, contents of both of which are incorporated herein by reference in their entireties.

TECHNICAL FIELD

The present disclosure relates to the field of medical imaging technologies, for example, to an information transmission method, apparatus, device and medium for medical imaging application.

BACKGROUND

Medical imaging application modules (such as pulse sequence, image reconstruction and post-processing methods of magnetic resonance imaging (MRI) or computed tomography (CT), etc.) are indispensable components of a medical imaging device.

Different users may have different application module requirements. For example, some users may require cardiac imaging application modules, while other users may require functional imaging application modules. Medical imaging devices with different versions may have different application configurations. For example, some imaging devices may be installed with the latest medical imaging pulse sequences or image reconstruction modules, while some imaging devices may only be installed with basic application modules. Medical imaging application modules in a medical imaging device can be installed by the device manufacturer or the users. Before an imaging device leaves the factory, the device manufacturer installs all the required medical imaging applications in the device with a software pre-installation manner. The upgrade of the medical imaging applications may be implemented in a manner of transmitting an upgrade package or a new installation package.

Clearly, the application upgrade or new application installation is implemented in a manual way. This makes the installation inconvenient. Furthermore, it is difficult to achieve effective application management for different devices.

SUMMARY

The present disclosure provides an information transmission method, apparatus, device and medium for medical imaging application, so as to implement automatic installation and upgrade of a medical imaging application corresponding to the imaging device, and effective management of medical imaging applications in the imaging device.

The present disclosure provides an information transmission method for medical imaging application, which includes steps described below.

An imaging device corresponding to an application authorization request is determined according to the received application authorization request, and an application permission profile of the imaging device is acquired; and a medical imaging application corresponding to the imaging device is determined according to the application permission profile of the imaging device, and medical imaging application information corresponding to the medical imaging application is transmitted to the imaging device.

The present disclosure further provides an information transmission apparatus for medical imaging application, which includes an application authorization module and an application information transmission module.

The application authorization module is configured to determine an imaging device corresponding to an application authorization request according to the received application authorization request, and acquire an application permission profile of the imaging device.

The application information transmission module is configured to determine the medical imaging applications corresponding to the imaging device according to the application permission profile of the imaging device, and transmit the information corresponding to the medical imaging applications to the imaging device.

The present disclosure further provides a information transmission device for medical imaging application, which includes at least one processor and a memory device.

The memory device is configured to store at least one program.

The at least one program, when executed by the at least one processor, causes the at least one processor to implement the information transmission method for medical imaging application according to any embodiment of the present disclosure.

The present disclosure further provides a computer readable storage medium, storing at least one program. The at least one program, when executed by a processor, implements the information transmission method for medical imaging application according to any embodiment of the present disclosure.

The present disclosure achieves automatic transmission of the information for medical imaging application suitable for the imaging device, and automatic download, installation and upgrade of the medical imaging application corresponding to the imaging device, which can reduce labor and time cost required for the installation of the medical imaging application, effectively manage medical imaging applications in the imaging device, thus reduce system maintenance cost of the imaging device.

DETAILED DESCRIPTION

Figure 1:
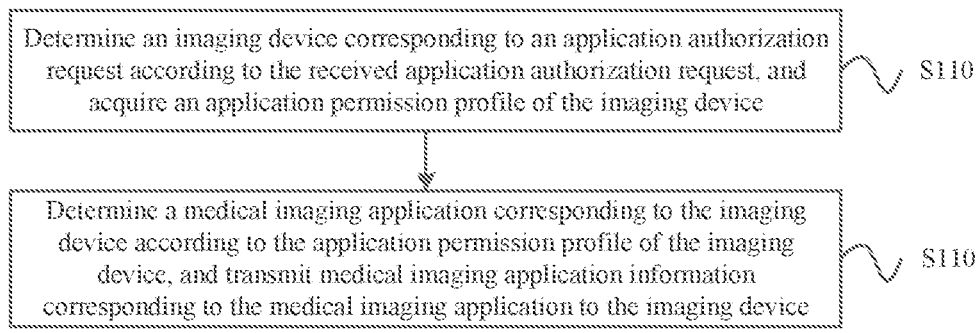
FIG. 1 is a flowchart of an information transmission method for medical imaging application according to an embodiment.

The present disclosure is described below with reference to the drawings and embodiments. The specific embodiments described in the present disclosure are only for illustration of the present disclosure and are not intended to limit the present disclosure. In addition, for convenience of description, only part of structures related to the present disclosure, not all of the structures, are shown in the drawings.

Embodiment One

FIG. 1 is a flowchart of an information transmission method for medical imaging application according to an embodiment. The present embodiment may be suitable to transmission of medical imaging applications to a medical imaging device to enable the medical imaging device to download, install and upgrade the medical imaging applications. The method may be executed by an information transmission apparatus for medical imaging application, which may be implemented in a manner of software and/or hardware. For example, the information transmission apparatus for medical imaging application may be arranged in an information transmission device for medical imaging application. As shown in FIG. 1, the method includes steps described below.

In step S110, an imaging device corresponding to an application authorization request is determined according to the received authorization access request, and the application permission profile of the imaging device is acquired.

In an embodiment, the imaging device may be any medical imaging device used for medical imaging, such as a magnetic resonance imaging (MRI) device, an X-ray computed tomography (CT) device, a digital X-ray imaging device, a nuclear imaging device, or an ultrasound imaging device. In the present embodiment, when it is necessary to install a medical imaging application in the imaging device or upgrade a medical imaging application existing in the imaging device, an imaging device user may enter an application store by clicking on an application store identifier on the imaging device. At this time, the imaging device transmits an authorization request for accessing the application store, i.e., an application authorization request. The application store determines the imaging device transmitting the application authorization request according to the received application authorization request. In an embodiment, the application authorization request transmitted by the imaging device includes a device identifier of the imaging device. The application store determines the imaging device transmitting the application authorization request according to the device identifier in the application authorization request.

In the present embodiment, the application store also needs to acquire an application permission profile of the imaging device transmitting the application authorization request. In an embodiment, after receiving the application authorization request transmitted by the imaging device, the application store may transmit an application permission acquisition instruction to the imaging device. The imaging device transmits the application permission profile stored in the imaging device to the application store according to the application permission acquisition instruction, and the application store acquires the application permission profile transmitted by the imaging device. In an embodiment, the imaging device may also transmit the application permission profile of the imaging device to the application store while transmitting the application authorization request.

In step S120, a medical imaging application corresponding to the imaging device is determined according to the application permission profile of the imaging device, and medical imaging application information corresponding to the medical imaging application is transmitted to the imaging device.

In an embodiment, medical imaging applications, which are compatible to imaging devices with different models and different types, are different. In order to facilitate an imaging device user to install a medical imaging application compatible to the imaging device on the imaging device, and to prevent an installed medical imaging application incompatible to the imaging device, the application store in this embodiment only transmits medical imaging application information compatible to the imaging device to the imaging device. In an embodiment, medical imaging application introduction information compatible to the imaging device may be transmitted to the imaging device first; when a view or download request triggered by the imaging device is detected, detailed information of the medical imaging application may be fed back according to the view or download request triggered by the imaging device.

In an embodiment, the application permission profile of the imaging device determines a medical imaging application available for the imaging device. At least one medical imaging application corresponding to the application permission profile is determined according to the application permission profile of the imaging device, and the determined medical imaging application is taken as the medical imaging application corresponding to the imaging device; then medical imaging application information corresponding to the imaging device is transmitted to the imaging device. In an embodiment, the application store may form an application list of medical imaging applications corresponding to the imaging device and display the application list through a front-end interactive interface of the application store on the imaging device, so that an imaging device user may browse, purchase, download or try the transmitted medical imaging application.

According to this embodiment, the medical imaging application information compatible to the imaging device is transmitted to the imaging device according to the application permission profile of the imaging device, so that the imaging device user may implement operations such as browsing, purchasing on the transmitted medical imaging application, the device manufacturer only needs to pre-install basic software when the imaging device leaves the factory, other customized software may be autonomously installed by an imaging device user through the application store; meanwhile when a medical imaging application on the imaging device needs to be installed or upgraded, medical imaging application information compatible to the imaging device will be automatically transmitted to the imaging device to complete the installation and upgrade of the medical imaging application corresponding to the imaging device. Labor and time cost required for the installation of the medical imaging application are therefore saved. Medical imaging applications in the imaging device can be effectively managed, so that system maintenance cost of the imaging device is reduced, and the rights and interests of software developers, device manufacturers and imaging device users are fully guaranteed.

The method further includes a step described below. A development request of a medical imaging application to be developed is received and the development request is released.

In a traditional medical imaging application development manner, it is difficult for medical imaging application developers to know the requirements of device manufacturers and imaging device users, and it takes a long time for device manufacturers and users to know the latest development progress. In the present embodiment, the device manufacturers and imaging device users may release the development requirements of medical imaging applications through the application store, the application store receives a development request of the medical imaging application to be developed and releases the development request on the front-end interactive interface. In an embodiment, the development requirements clearly specify the purposes, requirements, critical parameters and other information of the medical imaging application to be developed. The application developer may receive a current development requirement list through a message pushed by the application store, and selects a development project according to their own interests and proficiency to develop the medical imaging application to be developed in an application development environment provided by the device manufacturer.

In an embodiment, an application development requirement unit may be arranged in the front-end interactive interface of the application store for authorized device manufacturers or imaging device users to release medical imaging application development requirements, and/or for authorized application developers to browse medical imaging development requirements.

In an embodiment, the method further includes a step described below. A development progress of the medical imaging application to be developed is received and the development progress is displayed. In the present embodiment, an authorized application developer may also edit the development progress of the medical imaging application under development. In an embodiment, an authorized application developer may be any research or development entities authorized by the device manufacturers in the application store. In an embodiment, the development progress may be written by an application developer in a form of text editing, or may be selected by an application developer from an existing development progress menu. In an embodiment, the development progress may include a development stage, a debugging stage and so on.

In this embodiment, through receiving and releasing the development request and the development progress of the medical imaging application to be developed, the device manufacturers and imaging device users may release medical imaging application development requirements, know the development progress and latest achievements of the application developers efficiently, which also enables the application developers to learn requirements of the device manufacturers and imaging device users as soon as possible, so that time cost required for communication among various aspects can be reduced, and translation efficiency of the medical imaging application development can be improved.

Embodiment Two

Figure 2:
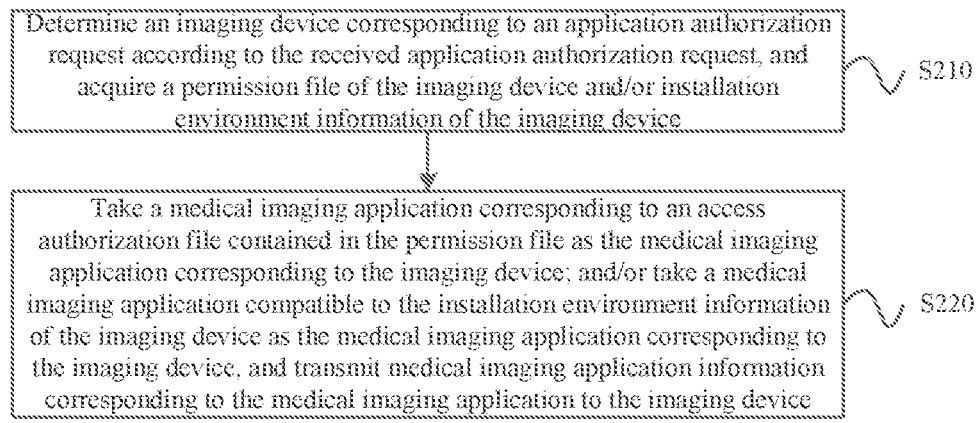
FIG. 2 is a flowchart of an information transmission method for medical imaging application according to another embodiment.

FIG. 2 is a flowchart of an imaging application information transmission method for medical imaging application according to another embodiment, which will be descried based on the above embodiment. As shown in FIG. 2, the method includes steps described below.

In step S210, an imaging device corresponding to an application authorization request is determined according to the received application authorization request, and at least one of a permission file of the imaging device or installation environment information of the imaging device is acquired.

In step S220, a medical imaging application corresponding to an access authorization file contained in the permission file is recorded in an application permission list of the imaging device; and/or a medical imaging application compatible to the installation environment of the imaging device is recorded in the application permission list of the imaging device, medical imaging application information corresponding to the medical imaging application is transmitted to the imaging device.

In this embodiment, the application permission profile of the imaging device is a permission file stored in the imaging device and/or the installation environment information of the imaging device, a medical imaging application to be transmitted is determined based on the permission file and/or the installation environment information of the imaging device.

In an embodiment, a permission certificate (i.e., the permission file) related to a medical imaging application is stored in the imaging device. At least one medical imaging application authorized by the imaging device is recorded in the permission file. The permission file authorizes the imaging device to enter the application store for browsing with restrictions, and the browsed subjects are within the medical imaging applications recorded in the permission file, so that a medical imaging application may be downloaded by an appropriate authorization device, and an imaging device user may view any medical imaging application provided in the application store according with the permission file through the front-end interactive interface of the application store on the imaging device. In an embodiment, the application store may acquire the permission file of the imaging device, as well as a medical imaging application subset in the application store corresponding to the permission file, and the acquired medical imaging application subset is displayed through the front-end interactive interface.

In the present embodiment, a medical imaging application corresponding to the medical imaging application information transmitted to the imaging device according to the permission certificate in the imaging device is a medical imaging application authorized to be used by the imaging device, that is, a medical imaging application that already exists in the imaging device and are permitted to be utilized. As may be seen that the medical imaging application to be transmitted is mainly used for updating or browsing an existing medical imaging application in the imaging device through the permission certificate in the imaging device.

In an embodiment, the medical imaging application to be transmitted may also be determined according to the installation environment information of the imaging device. In an embodiment, the installation environment information of the imaging device includes hardware information and software information. The hardware information is a hardware configuration of the imaging device, for example, the coil configuration, the CPU processing capability, etc. The software information is a software installation environment of the imaging device, such as a software installation environment including an underlying system version, a control version, language environment, etc. The application store determines a medical imaging application compatible to the imaging device according to the installation environment information of the imaging device, and the medical imaging application compatible to the installation environment information of the imaging device is taken as the medical imaging application corresponding to the imaging device, then the application store transmits the medical imaging application information corresponding to the medical imaging application to the imaging device. In the present embodiment, the medical imaging application to be transmitted determined by the installation environment information of the imaging device is a new application compatible to the imaging device.

For example, if an application developer completes and uploads a new application, which is a magnetic resonance vascular wall imaging application using a head-neck coil, the application information transmission condition of this application is a magnetic resonance apparatus equipped with a head-neck coil. If it is determined that a certain magnetic resonance apparatus is equipped with a head-neck coil, the magnetic resonance vascular wall imaging application using a head-neck coil is set to be compatible to the magnetic resonance device, and medical imaging application information corresponding to the medical imaging application is allowed to be transmitted to the magnetic resonance system.

Based on the above embodiments, the application permission profile of the imaging device is determined as the permission file stored in the imaging device and/or the installation environment information of the imaging device, and the medical imaging application information is transmitted based on the permission file and/or the installation environment information of the imaging device, so that installation or upgrade of medical imaging applications corresponding to different imaging devices is more accurate.

Embodiment Three

Figure 3:
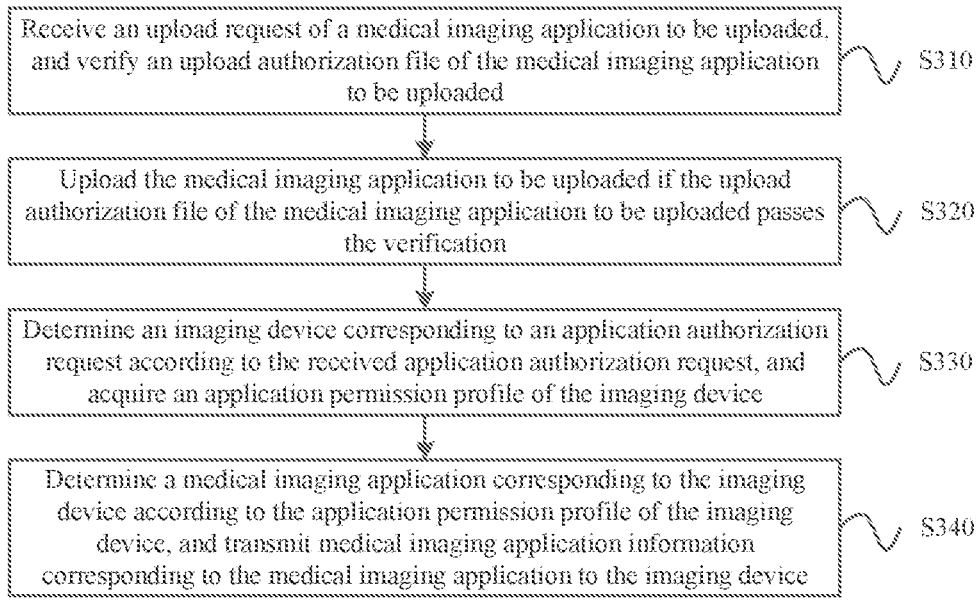
FIG. 3 is a flowchart of an information transmission method for medical imaging application according to another embodiment.

FIG. 3 is a flowchart of an information transmission method for medical imaging application according to another embodiment; which will be descried based on the above embodiments. As shown in FIG. 3, the method includes steps described below.

In step S310, an upload request of a medical imaging application to be uploaded is received, and an upload authorization file of the medical imaging application to be uploaded is verified.

In step S320, if the upload authorization file of the medical imaging application to be uploaded passes the verification, the medical imaging application to be uploaded is uploaded.

In this embodiment, after development of a new application is completed, the application developer may upload the medical imaging application verified by the device manufacturer in the application store. In an embodiment, the application developer may perform an upload operation of the medical imaging application on the front-end interactive interface of the application store; when the application developer triggers the upload operation, the application store receives an upload request of the medical imaging application to be uploaded. In the present embodiment, the upload request of the medical imaging application to be uploaded includes the medical imaging application to be uploaded and the upload authorization file of the medical imaging application to be uploaded. The application store verifies the upload authorization file of the medical imaging application to be uploaded, and the verified medical imaging application to be uploaded is automatically uploaded to the application store, so that the medical imaging application uploaded to the application store may be browsed and downloaded by an imaging device user.

In an embodiment, before the upload request of the medical imaging application to be uploaded is received, the method further includes steps described below. A check request of the medical imaging application to be checked is received, and a device manufacturer corresponding to the medical imaging application to be checked is determined; then the check request is pushed to the device manufacturer, so that the device manufacturer performs the check of the medical imaging application to be checked.

In the traditional application development manner, the application developer may bypass the manufacturer and go directly to the imaging device user to install the medical imaging application, which may cause some potential and uncontrollable hazards. In this embodiment, after an application developer develops a new medical imaging application, the medical imaging application needs to be uploaded to the application store for a corresponding device manufacturer to check, and the medical imaging application approved by the device manufacturer may be uploaded to the application store for imaging device users to browse.

In an embodiment, the check request of the medical imaging application to be checked includes the medical imaging application to be checked and a device manufacturer identifier corresponding to the medical imaging application to be checked. In an embodiment, if the medical imaging application to be checked corresponds to development requirements issued by a device manufacturer or an imaging device user, a device manufacturer corresponding to the medical imaging application to be checked may be determined according to the development requirements. If there is no correspondence between the medical imaging application to be checked and the development requirements, the application developer may be enabled to edit the device manufacturer corresponding to the medical imaging application to be checked while transmitting the check request, and the application store may acquire the device manufacturer corresponding to the medical imaging application to be checked from the check request.

In this embodiment, the application store transmits the check request of the medical imaging application to be checked to the corresponding device manufacturer, the device manufacturer performs the check of the medical imaging application to be checked, and transmits an upload authorization file issued for the medical imaging application passing the check to the application store, so that the application store transmits the upload authorization file to the application developer, thus the application developer transmits the upload request of the application to the application store while carrying the upload authorization file.

In step S330, an imaging device corresponding to an application authorization request is determined according to the received application authorization request, and an application permission profile of the imaging device is acquired.

In step S340, a medical imaging application corresponding to the imaging device is determined according to the application permission profile of the imaging device, and medical imaging application information corresponding to the medical imaging application is transmitted to the imaging device.

The present embodiment does not limit an order of an upload operation of the medical imaging application and transmission operation of the medical imaging application information to the imaging device according to the application permission profile of the imaging device. That is to say, operation steps in S310 and S320 according to this embodiment may be executed first to upload the medical imaging application, then operation steps in S330 and S340 according to this embodiment may be executed to complete the transmission of the medical imaging application information to the imaging device. It is also possible to execute the operation steps in S330 and S340 according to this embodiment to complete the transmission of the medical imaging application information to the imaging device first, then the operation steps in S310 and S320 according to this embodiment are executed to complete the upload of the medical imaging application.

The present embodiment adds the upload operation of the medical imaging application on the basis of the above embodiments, through reception of the upload request of the medical imaging application to be uploaded, the upload authorization file of the medical imaging application to be uploaded is verified. If the upload authorization file of the medical imaging application to be uploaded passes the verification, the medical imaging application to be uploaded is uploaded, so that only the medical imaging application passing the check by the device manufacturer may be browsed and used by imaging device users, thus it is ensured that the medical imaging application used by the imaging device users has passed permission and strict tests of the manufacturer, so that uncontrollable hazards can be avoided and the system maintenance cost is reduced.

The step in which the medical imaging application to be uploaded is uploaded includes steps described below. An access authorization file of the medical imaging application to be uploaded is formed according to permission information of the medical imaging application to be uploaded; and the access authorization file of the medical imaging application to be uploaded is uploaded.

In an embodiment, when the medical imaging application to be uploaded is uploaded to the application store, the access authorization file corresponding to the medical imaging application needs to be uploaded to the application store. In an embodiment, conditions under which the medical imaging application may be browsed and installed are recorded in the access authorization file, and only an imaging device compatible to the access authorization file is allowed to browse or install the medical imaging application. In an embodiment, the access authorization file may be formed by the permission information of the medical imaging application to be uploaded. For example, if it is recorded in permission information of the medical imaging application to be uploaded that the application is compatible to a magnetic resonance system equipped with a head-neck coil, the magnetic resonance system equipped with a head-neck coil is recorded into the authorization file. In an embodiment, a trial period of the medical imaging application may also be uploaded to the application store at the same time. The access authorization file of the medical imaging application to be uploaded and the medical imaging application to be uploaded are uploaded to the application store, transmission of the medical imaging application information may be performed according to the authorization file of the medical imaging application to be uploaded, so that the medical imaging application corresponding to the medical imaging application information transmitted to the imaging device is more suitable for the imaging device, and the transmission of the medical imaging application information is more accurate.

Embodiment Four

Figure 4:
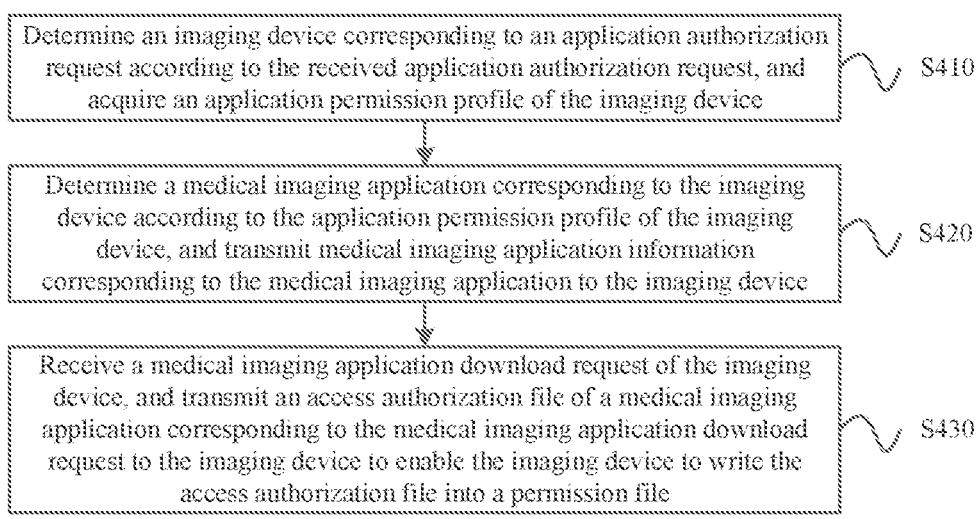
FIG. 4 is a flowchart of an information transmission method for medical imaging application according to another embodiment.

FIG. 4 is a flowchart of an information transmission method for medical imaging application according to another embodiment; which will be descried based on the above embodiments. As shown in FIG. 4, the method includes steps described below.

In step S410, an imaging device corresponding to an application authorization request is determined according to the received application authorization request, and an application permission profile of the imaging device is acquired.

In step S420, a medical imaging application corresponding to the imaging device is determined according to the application permission profile of the imaging device, and medical imaging application information corresponding to the medical imaging application is transmitted to the imaging device.

In step S430, a medical imaging application download request of the imaging device is received, and an access authorization file of a medical imaging application corresponding to the medical imaging application download request is transmitted to the imaging device to enable the imaging device to write the access authorization file into a permission file.

In the present embodiment, after the medical imaging application information compatible to the imaging device is transmitted to the imaging device, an imaging device user may browse medical imaging applications in the medical imaging application list and download an interested medical imaging application. When the imaging device user triggers a download operation of a certain medical imaging application through the front-end interactive interface of the application store on the imaging device, the application store receives an application download request transmitted by the imaging device and checks the application download request; if the application download request passes the check, the imaging device is allowed to download and install the medical imaging application, and the access authorization file of the medical imaging application is transmitted to the imaging device, so that the imaging device writes the access authorization file into the permission file, so as to use the downloaded medical imaging application.

In an embodiment, the application download request of the medical imaging application includes a trial request and a purchase request. If a user wants to try a certain medical imaging application, a trial operation of the medical imaging application is triggered through the front-end interactive interface of the application store. The application store checks a trial request after receiving the trial request. If the trial request passes the check, the access authorization file and the trial period of the medical imaging application are transmitted to the imaging device, so that the imaging device writes the access authorization file and the trial period into the permission file, and the installed medical imaging application may be used. If the trial period of the medical imaging application expires, the access authorization file in the permission file of the imaging device is automatically deleted, the medical imaging application is unavailable after the access authorization file is deleted.

In an embodiment, if the received download request of the medical imaging application is the purchase request, after the user completes a purchase operation, a state of the medical imaging application of the imaging device is detected, and a corresponding operation is executed according to the state of the medical imaging application, so that the imaging device updates the access authorization file in the permission file. In an embodiment, the manner of purchasing a medical imaging application by a user is not limited, for example, the medical imaging application may be purchased by a check, a bank transfer, etc.

In an embodiment, the state of the medical imaging application may be uninstalled, on-trial, or trial period expired. If the medical imaging application is uninstalled or the trial period expires, the access authorization file of the medical imaging application is directly transmitted to the imaging device, so that the imaging device writes the access authorization file into the permission file. If the state of the medical imaging application is on-trial, a control instruction is transmitted to the imaging device, so the imaging device is controlled to delete lifetime in the permission file.

Based on the above embodiments, operations of receiving the medical imaging application download request of the imaging device and transmitting the access authorization file of the medical imaging application corresponding to the application download request to the imaging device are added, so that the medical imaging application corresponding to the imaging device is installed or upgraded according to requirements of an imaging device user, and more accurate installation or upgrade service of the medical imaging application is provided for imaging device users.

The method further includes steps described below.

Feedback information of the medical imaging application is received, and the feedback information is pushed to an application developer and/or a device manufacturer.

In an embodiment, the imaging device user may also perform feedback of the medical imaging application through the application store, and the user may edit opinions and suggestions through the front-end interactive interface of the application store during trial and use, so that feedback of the medical imaging application is realized.

Embodiment Five

Figure 5:
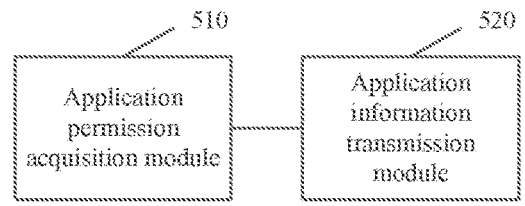
FIG. 5 is a schematic structural diagram of an information transmission apparatus for medical imaging application according to an embodiment.

FIG. 5 is a schematic structural diagram of an information transmission apparatus for medical imaging application according to an embodiment. The information transmission apparatus for medical imaging application may be implemented in a manner of software and/or hardware, for example, the information transmission apparatus for medical imaging application may be arranged in an information transmission device for medical imaging application, as shown in FIG. 5, the apparatus includes an application permission acquisition module 510 and an application information transmission module 520. The application permission acquisition module 510 is configured to determine an imaging device corresponding to an application authorization request according to the received application authorization request, and acquire an application permission profile of the imaging device. The application information transmission module 520 is configured to determine a medical imaging application corresponding to the imaging device according to the application permission profile of the imaging device, and transmit medical imaging application information corresponding to the medical imaging application to the imaging device.

In the present embodiment, the application information transmission module determines the imaging device corresponding to the application authorization request according to the received application authorization request, and acquires the application permission profile of the imaging device; and the application information transmission module determines the medical imaging application corresponding to the imaging equipment according to the application permission profile of the imaging device, and transmits the medical imaging application information corresponding to the medical imaging application to the imaging device, which will realize automatic transmission of the medical imaging application information compatible to the imaging device, so that installation and upgrade of the medical imaging application corresponding to the imaging device can be automatically completed, the labor and time cost required for the installation of the medical imaging application are saved, medical imaging applications in the imaging device can be effectively managed, and the system maintenance cost of the imaging device is reduced.

The application permission acquisition module 510 is configured to acquire the application permission profile of the imaging device in a following manner: the imaging device corresponding to the application authorization request is determined according to the received application authorization request, and at least one of a permission file of the imaging device or installation environment information of the imaging device is acquired.

The application information transmission module 520 is configured to determine the medical imaging application corresponding to the imaging device according to the application permission profile of the imaging device in following manners: a medical imaging application corresponding to an access authorization file contained in the permission file is recorded in an application permission list of the imaging device; and/or a medical imaging application compatible to the installation environment information of the imaging device is recorded in the application permission list of the imaging device.

The apparatus further includes an upload authorization verification module and an application upload module. The upload authorization verification module is configured to receive an upload request of a medical imaging application to be uploaded, and verify an upload authorization file of the medical imaging application to be uploaded; and the application upload module is configured to upload the medical imaging application to be uploaded, when the upload authorization file of the medical imaging application to be uploaded passing the verification.

The application upload module includes an access authorization formation unit and an access authorization upload unit. The access authorization formation unit is configured to form an access authorization file of the medical imaging application to be uploaded according to attribute information of the medical imaging application to be uploaded; and the access authorization upload unit is configured to upload the access authorization file of the medical imaging application to be uploaded.

The apparatus further includes a download request response module. The download request response module is configured to receive a medical imaging application download request of the imaging device, and transmitting an access authorization file of a medical imaging application corresponding to the medical imaging application download request to the imaging device to enable the imaging device to write the access authorization file into a permission file, after the medical imaging application information corresponding to the medical imaging application is transmitted to the imaging device.

The apparatus further includes a development request release module. The development request release module is configured to receive a development request of a medical imaging application to be developed, and release the development request.

The information transmission apparatus for medical imaging application provided in this embodiment can execute the information transmission method for medical imaging application provided in any embodiment, and the apparatus has corresponding functional modules for execution of the method and beneficial effects of execution of the method.

Embodiment Six

Figure 6:
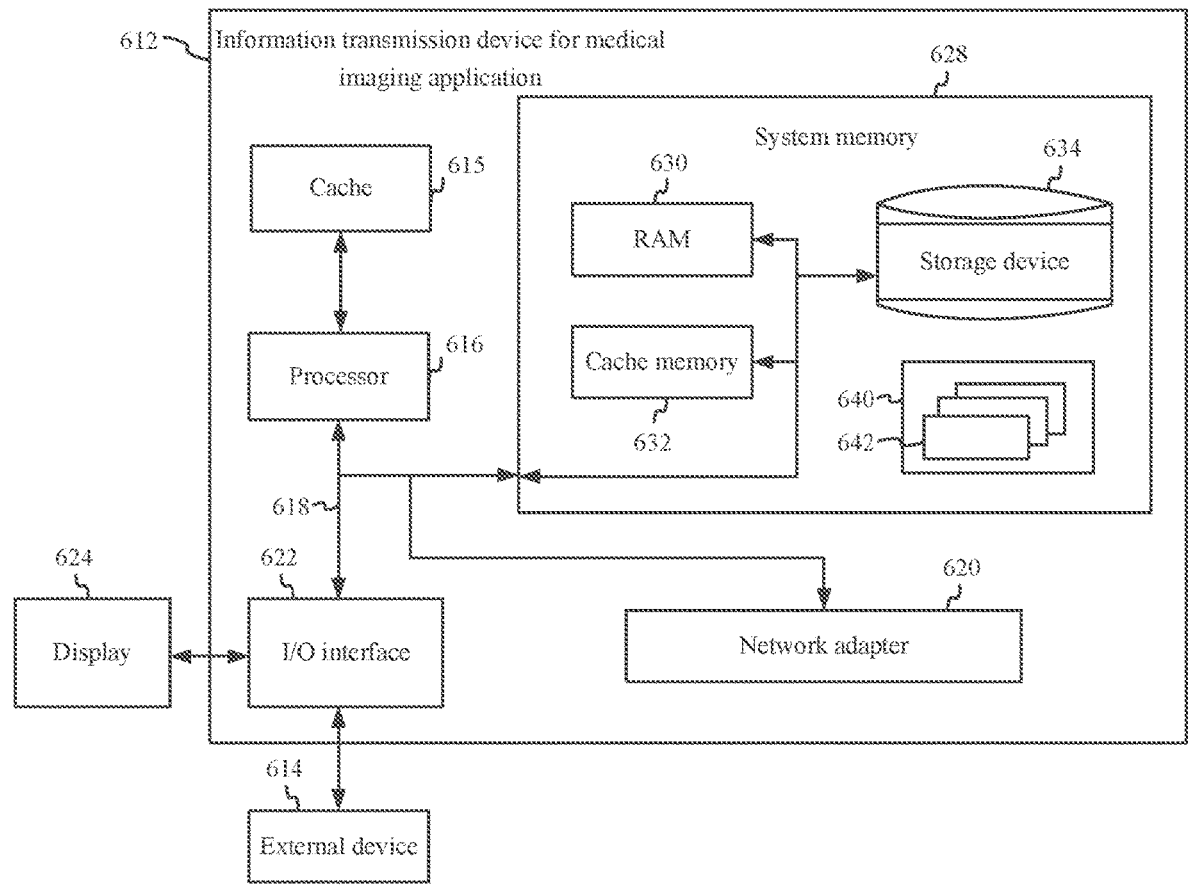
FIG. 6 is a schematic structural diagram of an information transmission device for medical imaging application according to an embodiment.

FIG. 6 is a schematic structural diagram of an information transmission device for medical imaging application according to an embodiment. FIG. 6 shows an exemplary block diagram of an information transmission device 612 for medical imaging application suitable for implementing embodiments of the present disclosure. The information transmission device 612 for medical imaging application shown in FIG. 6 is only an example and should not impose any restrictions on functions and a use scope of the embodiments of the present disclosure.

As shown in FIG. 6, the information transmission device 612 for medical imaging application is represented in the form of a general-purpose computing device. The information transmission device 612 for medical imaging application may include components, but are not limited to, at least one processor 616, a system memory 628, and a bus 618 for connecting different system components (including the system memory 628 and the processor 616).

The bus 618 represents at least one of several types of bus structures, including a memory bus, a memory controller, a peripheral bus, a graphics acceleration port, a processor 616, or a local bus using any of a variety of bus structures. For example, these structures include, but are not limited to, an industry subversive alliance (ISA) bus, a micro channel architecture (MAC) bus, an enhanced ISA bus, a video electronics standards association (VESA) local bus, and a peripheral component interconnect (PCI) bus.

The information transmission device 612 for medical imaging application includes various computer system readable media. These media may be any available medium that may be accessed by the information transmission device 612 for medical imaging application, including a volatile medium, a non-volatile medium, a removable medium and a non-removable media.

The system memory 628 may include a computer system readable medium in the form of a volatile memory, such as a random access memory (RAM) 630 and/or a cache memory 632. The information transmission device 612 for medical imaging application may include other removable/non-removable, volatile/non-volatile computer system storage media. Only for example, a storage device 634 may be configured to read from and write into a non-removable, non-volatile magnetic medium (not shown in FIG. 6, which is commonly referred to as a "hard disk drive"). Although it is not shown in FIG. 6, a magnetic disk drive configured to read from or write into a removable non-volatile magnetic disk (e.g., "a floppy disk") and an optical disc drive configured to read from or write into a removable non-volatile optical disk (e.g., a compact disc read-only memory (CD-ROM), a digital video disc read-only memory (DVD-ROM), or other optical media) may be provided. In these cases, each drive may be connected to the bus 618 through one or more data media interfaces. The memory 628 may include at least one program product, the program product includes a set (e.g., at least one) of program modules configured to execute functions of any embodiments of the present disclosure.

Programs/utilities 640 with a set (at least one) of program modules 642 may be, for example, stored in the memory 628, these program modules 642 may include, but not limited to, an operating system, one or more application programs, other program module, and program data, each or some combination of these examples may include an implementation of a network environment. The program modules 642 usually perform functions and/or methods of the embodiments described in the present disclosure.

The information transmission device 612 for medical imaging application may also communicate with one or more external devices 614 (e.g., a keyboard, a pointing device, a display 624, etc.), may also communicate with one or more devices that enables a user to interact with the information transmission device 612 for medical imaging application, and/or any device (e.g., a network card, a modem, etc.) that enables the information transmission device 612 for medical imaging application to communicate with one or more other computing devices. This communication may be performed through an input/output (I/O) interface 622. Furthermore, the information transmission device 612 for medical imaging application may also communicate with one or more networks (e.g., a local area network (LAN), a wide area network (WAN), and/or a public network such as the Internet) through a network adapter 620. As shown in the figure, the network adapter 620 communicates with other modules of the information transmission device 612 for medical imaging application through the bus 618. Although it is not shown in FIG. 6, other hardware and/or software modules may be used in combination with the information transmission device 612 for medical imaging application, including but not limited to micro codes, a device driver, a redundant processing unit, an external disk drive array, a RAID system, a tape drive, a data backup storage system, and so on.

The processor 616 executes at least one functional application and data processing by execution of a program stored in the system memory 628, for example, to realize the information transmission method for medical imaging application provided by the embodiments of the present disclosure. The method includes steps described below. An imaging device corresponding to an application authorization request is determined according to the received application authorization request, and an application permission profile of the imaging device is acquired; a medical imaging application corresponding to the imaging device is determined according to the application permission profile of the imaging device, and medical imaging application information corresponding to the medical imaging application is transmitted to the medical imaging application of the imaging device.

The processor may also implement the information transmission method for medical imaging application provided by any embodiments of the present disclosure.

Embodiment Seven

The embodiments provide a computer readable storage medium, which stores a computer program, when the computer program is executed by a processor, it implements the information transmission for medical imaging application provided by the embodiments of the present disclosure. The method includes steps described below. An imaging device corresponding to an application authorization request is determined according to the received application authorization request, and an application permission profile of the imaging device is acquired; and a medical imaging application corresponding to the imaging device is determined according to the application permission profile of the imaging device, and medical imaging application information corresponding to the medical imaging application is transmitted to the imaging device.

The present embodiment provides a computer readable storage medium, the computer program stored on the computer readable storage medium is not limited to operations of the methods described above, but may also perform related operations in the information transmission method for medical imaging application provided by any embodiment of the present disclosure.

The computer storage medium of this embodiment may use any combination of one or more computer readable media. The computer readable medium may be a computer readable signal medium or a computer readable storage medium. The computer readable storage medium may be, for example, but not limited to, an electrical, magnetic, optical, electromagnetic, infrared, or semiconductor system, apparatus, or device, or any combination thereof. Examples (a non-exhaustive list) of the computer readable storage medium include: an electrical connection having one or more wires, a portable computer disk, a hard disk, a RAM, a read-only memory (ROM), an erasable programmable read-only memory (EPROM) or a flash memory, an optical fiber, a CD-ROM, an optical storage device, a magnetic storage device, or any suitable combination of the above. In the present disclosure, the computer readable storage medium may be any tangible medium containing or storing at least one program that may be used by or in combination with an instruction execution system, apparatus, or device.

The computer readable signal medium may include a data signal propagated in baseband or as part of a carrier wave, on which a computer readable program code is carried. This propagated data signal may have many forms, including, but not limited to, an electromagnetic signal, an optical signal, or any suitable combination of the above signals. The computer readable signal medium may also be any computer readable medium other than the computer readable storage medium, which may transmit, propagate, or transport a program for use by or in connection with an instruction execution system, apparatus, or device.

The program code contained in the computer readable medium may be transmitted using any suitable medium, including, but not limited to, wireless, wire, fiber optic cable, radio frequency (RF), etc., or any suitable combination of the above manners.

Computer program codes for executing operations of the present disclosure may be written in one or more programming languages or a combination of multiple programming languages, including object-oriented programming languages, such as Java, Smalltalk, C++, and conventional procedural programming languages such as "c" language or similar programming languages. The program codes may be completely executed on a user computer, partially executed on the user computer, executed as a separate software package, partially executed on the user computer, partially executed on a remote computer, or completely executed on a remote computer or server. In a case where a remote computer is involved, the remote computer may be connected to the user computer through any kind of network, including a LAN or WAN, or the remote computer may be connected to an external computer (e.g., via the Internet using an Internet service provider).

What is claimed is:

1. A information transmission method for medical imaging application, comprising:
   determining an imaging device corresponding to an application authorization request according to the received application authorization request, and acquiring an access authorization file in an application permission list of the imaging device; wherein the access authorization file records at least one medical imaging application authorized by the imaging device; and
   recording a medical imaging application corresponding to the access authorization file, and transmitting medical imaging application information corresponding to the medical imaging application to the imaging device for the imaging device to install or upgrade the medical imaging application;
   wherein the method further comprises:
   receiving a development request of a medical imaging application to be developed, and displaying the development request; and
   receiving a development progress of the medical imaging application to be developed, and displaying the development progress.

2. The method according to claim 1, wherein the method further comprises:
   acquiring installation environment information of the imaging device.

3. The method according to claim 2, wherein the method further comprises:
   recording a medical imaging application compatible to the installation environment information of the imaging device in the application permission list of the imaging device.

4. The method according to claim 1, further comprising:
   receiving an upload request of a medical imaging application to be uploaded, and verifying an upload authorization file of the medical imaging application to be uploaded; and
   in response to the upload authorization file of the medical imaging application to be uploaded passing the verification, uploading the medical imaging application to be uploaded.

5. The method according to claim 4, wherein uploading the medical imaging application to be uploaded comprises:
   forming an access authorization file of the medical imaging application to be uploaded according to attribute information of the medical imaging application to be uploaded; and
   uploading the access authorization file of the medical imaging application to be uploaded.

6. The method according to claim 1, wherein after transmitting the medical imaging application information corresponding to the medical imaging application to the imaging device, the method further comprises:
   receiving a medical imaging application download request of the imaging device, and transmitting an access authorization file of a medical imaging application corresponding to the medical imaging application download request to the imaging device to enable the imaging device to write the access authorization file into a permission file.

7. The method according to claim 6, wherein the medical imaging application download request comprises a trial request, and transmitting the access authorization file of the medical imaging application corresponding to the medical imaging application download request to the imaging device to enable the imaging device to write the access authorization file into the permission file comprises:
   checking the trial request, and in response to the trial request passing the check, transmitting the access authorization file and a trial period of the medical imaging application corresponding to the trial request to the imaging device to enable the imaging device to write the access authorization file and the trial period into the permission file.

8. The method according to claim 6, wherein the medical imaging application download request comprises a purchase request, and transmitting the access authorization file of the medical imaging application corresponding to the medical imaging application download request to the imaging device to enable the imaging device to write the access authorization file into the permission file comprises:
  in a case where a purchase operation of the purchase request is detected, updating the access authorization file in the permission file of the imaging device according to a state of the medical imaging application in the imaging device.

9. The method according to claim 4, wherein the upload request comprises an upload authorization file;
  wherein before receiving the upload request of the medical imaging application to be uploaded, the method further comprises:
  receiving a check request of a medical imaging application to be checked, and determining a device manufacturer corresponding to the medical imaging application to be checked; and
  pushing the check request to the device manufacturer, and receiving an upload authorization file issued by the device manufacturer for the medical imaging application to be checked.

10. An information transmission device for medical imaging application, comprising:
  at least one processor; and
  a storage device, which is configured to store at least one program;
  wherein the at least one program, when executed by the at least one processor, causes the at least one processor to:
  determine an imaging device corresponding to an application authorization request according to the received application authorization request, and acquire an access authorization file in an application permission list of the imaging device; wherein the access authorization file records at least one medical imaging application authorized by the imaging device; and
  record a medical imaging application corresponding to the access authorization file, and transmit medical imaging application information corresponding to the medical imaging application to the imaging device for the imaging device to install or upgrade the medical imaging application;
  wherein the at least one processor is further caused to:
  receive a development request of a medical imaging application to be developed, and display the development request; and
  receive a development progress of the medical imaging application to be developed, and display the development progress.

11. A non-transitory computer readable storage medium, storing at least one computer program, wherein the at least one computer program, when executed by a processor, implements an information transmission method for medical imaging application,
  wherein the method comprises:
  determining an imaging device corresponding to an application authorization request according to the received application authorization request, and acquiring an access authorization file in an application permission list of the imaging device; wherein the access authorization file records at least one medical imaging application authorized by the imaging device; and
  recording a medical imaging application corresponding to the access authorization file, and transmitting medical imaging application information corresponding to the medical imaging application to the imaging device for the imaging device to install or upgrade the medical imaging application;
  wherein the method further comprises:
  receiving a development request of a medical imaging application to be developed, and displaying the development request; and
  receiving a development progress of the medical imaging application to be developed, and displaying the development progress.

12. The method according to claim 2, further comprising:
  receiving an upload request of a medical imaging application to be uploaded, and verifying an upload authorization file of the medical imaging application to be uploaded; and
  in response to the upload authorization file of the medical imaging application to be uploaded passing the verification, uploading the medical imaging application to be uploaded.

13. The method according to claim 3, further comprising:
  receiving an upload request of a medical imaging application to be uploaded, and verifying an upload authorization file of the medical imaging application to be uploaded; and
  in response to the upload authorization file of the medical imaging application to be uploaded passing the verification, uploading the medical imaging application to be uploaded.

14. The method according to claim 2, wherein after transmitting the medical imaging application information corresponding to the medical imaging application to the imaging device, the method further comprises:
  receiving a medical imaging application download request of the imaging device, and transmitting an access authorization file of a medical imaging application corresponding to the medical imaging application download request to the imaging device to enable the imaging device to write the access authorization file into a permission file.

15. The method according to claim 3, wherein after transmitting the medical imaging application information corresponding to the medical imaging application to the imaging device, the method further comprises:
  receiving a medical imaging application download request of the imaging device, and transmitting an access authorization file of a medical imaging application corresponding to the medical imaging application download request to the imaging device to enable the imaging device to write the access authorization file into a permission file.

16. The method according to claim 4, wherein after transmitting the medical imaging application information corresponding to the medical imaging application to the imaging device, the method further comprises:
  receiving a medical imaging application download request of the imaging device, and transmitting an access authorization file of a medical imaging application corresponding to the medical imaging application download request to the imaging device to enable the imaging device to write the access authorization file into a permission file.

17. The method according to claim 5, wherein after transmitting the medical imaging application information corresponding to the medical imaging application to the imaging device, the method further comprises:
  receiving a medical imaging application download request of the imaging device, and transmitting an access authorization file of a medical imaging application corresponding to the medical imaging application download request to the imaging device to enable the imaging device to write the access authorization file into a permission file.

18. The method according to claim 5, wherein the upload request comprises an upload authorization file;
wherein before receiving the upload request of the medical imaging application to be uploaded, the method further comprises:
receiving a check request of a medical imaging application to be checked, and determining a device manufacturer corresponding to the medical imaging application to be checked; and
pushing the check request to the device manufacturer, and receiving an upload authorization file issued by the device manufacturer for the medical imaging application to be checked.

19. The device according to claim 10, wherein the at least one processor is further caused to:
acquire installation environment information of the imaging device.

20. The device according to claim 19, wherein the at least one processor is further caused to:
record a medical imaging application compatible to the installation environment information of the imaging device in the application permission list of the imaging device.

* * * * *